United States Patent [19]

Sandholm

[11] Patent Number: 4,659,656
[45] Date of Patent: Apr. 21, 1987

[54] METHOD OF DETECTING MASTITIS IN COWS

[75] Inventor: Markus Sandholm, Helsinki, Finland

[73] Assignees: Labsystems Oy; Eflab Oy, both of Helsinki, Finland

[21] Appl. No.: 620,157

[22] Filed: Jun. 13, 1984

[51] Int. Cl.$^4$ .................... G01N 33/53; C12Q 1/38
[52] U.S. Cl. ............................. 435/7; 435/23
[58] Field of Search ........................ 435/7, 23

[56] References Cited

U.S. PATENT DOCUMENTS

| | | | |
|---|---|---|---|
| 3,926,732 | 12/1975 | Rosen et al. | 435/28 |
| 4,425,330 | 1/1984 | Norcross et al. | 424/88 |

OTHER PUBLICATIONS de Rham et al., J. Dairy Res. (1982) 49, 587-596.
Honkanen-Buzalski et al., J. Dairy Res. (1981) 48, 213-23.
Honkanen-Buzalski et al., Chemical Abstracts, 96 (1982) #140648z.
Sandholm et al., Chemical Abstracts 100 (1984) #47513t.

Primary Examiner—Christine M. Nucker
Attorney, Agent, or Firm—Hopgood, Calimafde, Kalil, Blaustein & Judlowe

[57] ABSTRACT

There is disclosed a method for the quantitative determination of mastitis in a cow. This method comprises decaseinating and delipidating a milk sample from the cow to obtain a clear solution, substantially removing $\alpha_2$-macroglobulin from the sample, mixing the clear and substantially $\alpha_2$-macroglobulin free sample with a known amount to trypsin, and measuring the activity of the amount of trypsin which is in excess of the amount which is inactivated by the milk's antitrypsin.

4 Claims, 6 Drawing Figures

METHOD OF DETECTING MASTITIS IN COWS

CROSS REFERENCE TO RELATED APPLICATION

This application discloses subject matter which is common to and disclosed in an application entitled "Method For The Detection of Inflammation of the Udder," filed currently herewith by Markus Sandholm. The entire disclosure of the concurrently filed application is hereby incorporated by reference.

BACKGROUND OF THE INVENTION

The present invention is directed generally to a method for the quantitative determination of mastitis, an inflammation of the udder of a cow. The method is based upon measuring the increased trypsin-inactivating effect of milk.

Mastitis, as an inflammatory process, produces an increased permeability between the blood and milk compartments, resulting in extravasation of plasma proteins, including $\alpha_1$-antitrypsin, into the milk, which produces the increased trypsin-inactivating effect.

The more important methods currently used for determining and detecting inflammation of the udder are based on bacteriology and on the determination of the number of cells in a milk sample.

These methods are disadvantageous since the apparatus required for determining and counting the cells is expensive, difficult to use, and requires substantial maintenance. Furthermore, this apparatus is available only at the largest research laboratories of the dairy industry. Also, storage of milk samples for counting and determining the cells is technically inconvenient and requires special operations. The number of cells measured from the milk sample may be influenced by factors other than the disease, depending on the time and mode of taking the sample. Finally, it has not been possible to reliably perform an inter-teat examination for detecting mastitis. Thus, the detection of latent inflammation of the udder has been highly uncertain.

The search has continued for new and improved methods of determining mastitis. This invention was made as a result of that search.

OBJECTS AND SUMMARY OF THE INVENTION

Accordingly, it is a general object of the present invention to avoid or substantially alleviate the above-described problems of prior art methods.

A more specific object of the present invention is to provide a process for determining mastitis based upon a colorimetric reaction.

Another object of the present invention is to provide a process of quantitatively determining the amount of antitrypsin in a milk sample.

Other objects and advantages of the present invention will become clear from the following summary of the invention and description of the preferred embodiments.

The present invention provides a method for the quantitative determination of mastisis in cows. This method comprises decaseinating and delipidating a milk sample from the cow to obtain a clear solution, substantially removing the $\alpha_2$-macroglobulin from the sample, preferably by polyethylene glycol precipitation, mixing the clear and substantially $\alpha_2$-macroglobulin free sample with a known amount of trypsin, and measuring the activity of the amount of trypsin which is in excess of that which remains in the sample after inactivation with antitrypsin.

The advantages of the present method are as follows:

(1) The assay measures the concentration of a small molecular weight blood protein in milk which is a good marker for increased permeability between blood and milk compartments due to the inflammation.

(2) The evaluation of the results is easier than that from the somatic cell count. Milk antitrypsin, like Bovine Serum Albumin (BSA), is only slightly affected by the lactation number. Also, the daily variation in milk antitrypsin is much smaller than that for the somatic cell count (% variation).

(3) The sampling does not require strict asepsis. The samples may be stored for longer periods by freezing or using additives, such as sodium azide.

(4) The assay is cheap. No immunologic reagents are required.

(5) The capacity of the system is high and may be automated.

(6) Systematic inter-teat evaluation becomes easier. The confusion of individual quarters is minimized. No labelling is required for the individual quarters.

The method of the present invention is based on the observation of an increased permeability associated with the disease. In a diseased cow, small molecular weight proteins, such as blood albumin and $\alpha 1$-antitrypsin leak into the milk.

Two problems are generally encountered when relying on the concentration of blood-derived proteins in milk for large scale mastitis analysis; first, deciding which particular blood protein in milk is correlated with the severity of inflammation; and second, choosing one of such proteins to be analyzed by simple automated procedures, with a reliable method for large-scale monitoring programms. The antitrypsin activity in post-colostral milk is serum-derived. Alpha$_1$-protease inhibitor and $\alpha_2$-macroglobulin ($\alpha_2$M) are mainly responsible for the antitrypsin activity in milk.

Milk antitrypsin is a sensitive indicator of mastisis. As a result of this observation, the colorimetric procedure of the present invention was developed for large-scale monitoring of milk activity.

BRIEF DESCRIPTION OF THE DRAWINGS

For a fuller understanding of the invention, reference is had to the following description in connection with the accompanying drawings in which.

DESCRIPTION OF THE PREFERRED EMBODIMENT

Theoretically, the antitrypsin activity in milk could be analyzed simply by mixing milk with a known amount of trypsin and measuring the activity of trypsin-excess by a colorimetic procedure using a synthetic substrate such as BAPNA. There are several matters to be resolved before the colorimetric procedure could be adapted to milk samples for further automation. The milk should be decaseinated and delapidating to obtain clear base-solutions. The $\alpha_2M$ present in milk causes another problem. Even $\alpha_2M$ if binds trypsin, the proteolytic activity towards small molecular weight substrates, such as BAPNA, is retained. Therefore $\alpha_2M$ should be removed at the same step as the casein and cream. This was successfully undertaken by polyethylene glycol precipitation. The present invention describes an automated method based on milk antitrypsin.

SOLUTIONS

Clearing solution: 16.7% polyethylene glycol (PEG-6000) and 1% dimethylformamide in 0.1 M TRIS-0.02 M $CaCl_2$ buffer, pH=8.2.

Trypsin: Stock solution: 50 mg trypsin in 100 ml 1 mM HCl. The working solution (2.5 ug/ml) is prepared daily by diluting the stock solution 1 to 200 in 1 mM HCl.

BAPNA-substrate: 100 mg of N-benzoylarginine-p-nitroanilide is dissolved in 100 ml distilled water in a water bath (95° C.) and cooled to room temperature.

PREPARATION OF MILK SAMPLES

The milk samples are mixed with two volumes of the clearing solution, mixed and left to stand at room temperature for 30 minutes, after which they become clear by centrifugation (10,000 g/1 min). This way the casein, cream and $\alpha_2M$ are co-precipitated leaving the $\alpha_1$-protease-inhibitor in the supernate.

ASSAY

Figure 1:
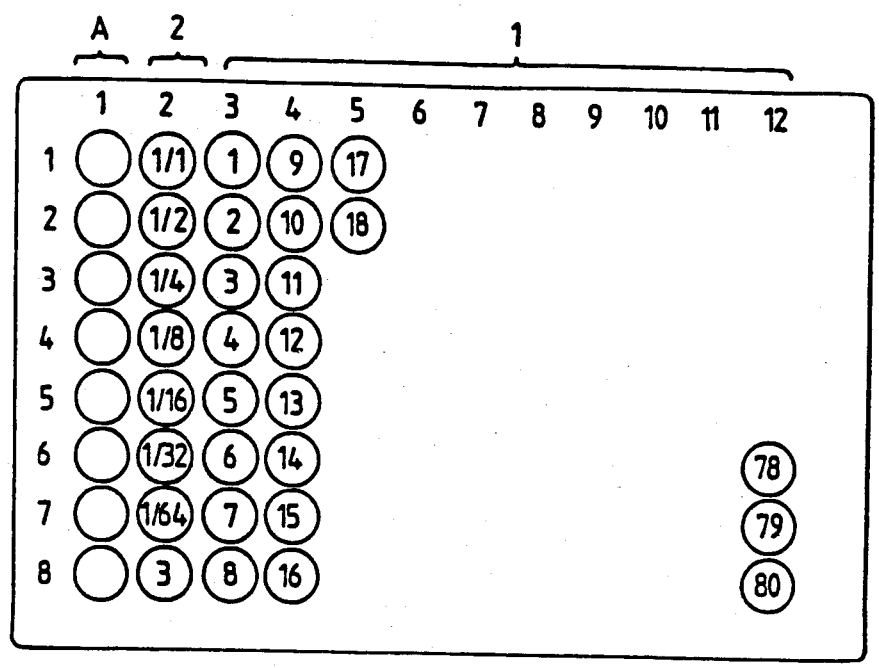
FIG. 1 is a top view of a microtiter plate used in the method of the invention.
Figure 2:
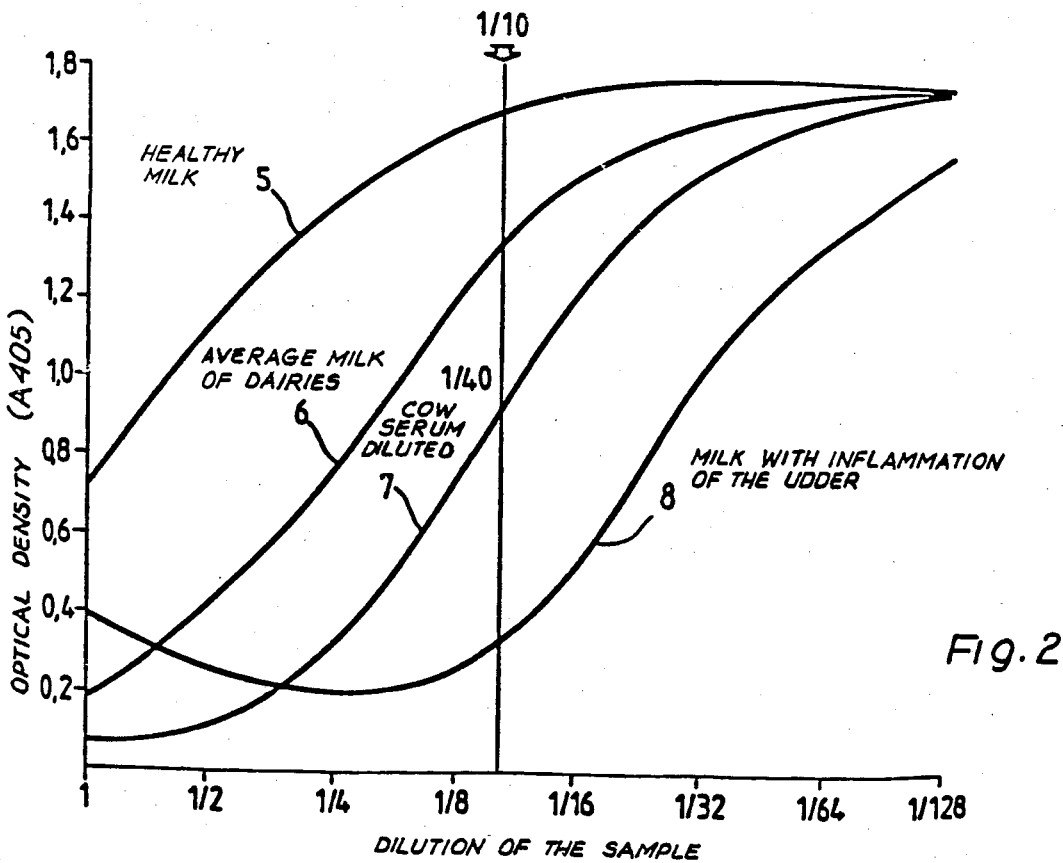
FIG. 2 is a graphical presentation of the results obtained through the use of the method of the invention.
Figure 3:
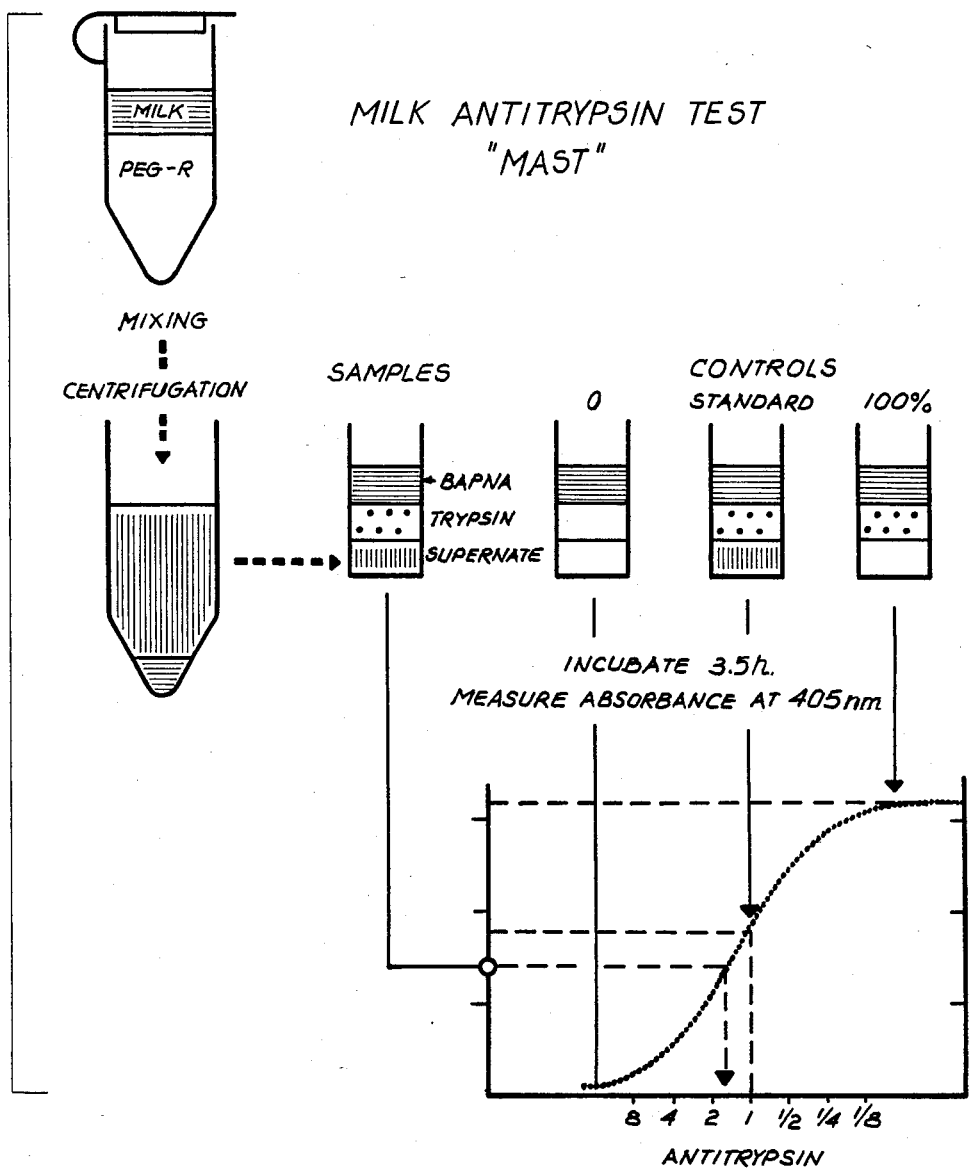
FIG. 3 illustrates the principle of the milk antitrypsin assay. The milk is precipitated with the clearing solution. The supernate is mixed with trypsin, upon which a part of the trypsin becomes inactivated by the antitrypsin present in milk. The excess trypsin releases a chromogen from N-benzoylarginine-p-nitroanilide (BAPNA) which is measured by adsorption at 405 nm. By including the 100% control (without any antitrypsin) and 0% blank (without any trypsin), a computer-fit program may be formed. The computer reads the absorbence for the standard samples and correlates the remainder.
Figure 4:
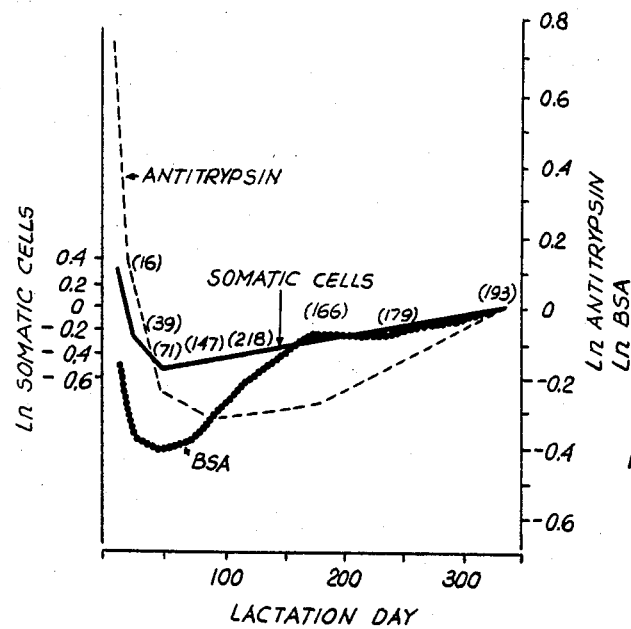
FIG. 4 illustrates milk antitrypsin, somatic cell counts and albumin (BSA) at different stages of lactation. The curves have been drawn from material consisting of 1029 cow samples and analyzing the effect of lactation stage by the least square analysis. The curves have been drawn using deviations from the last class mean adjusting the scales to the same standard deviation.
Figure 5:
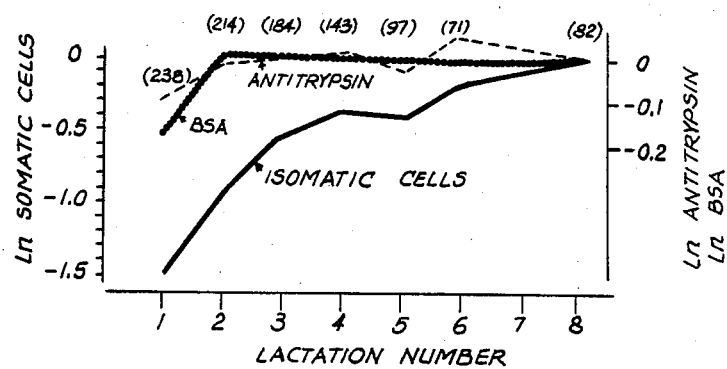
FIG. 5 illustrates milk antitrypsin, somatic cell counts and albumin (BSA) as affected by the lactation number. The somatic cell content increases with increasing lactation number but BSA and antitrypsin are influenced minimally.
Figure 6:
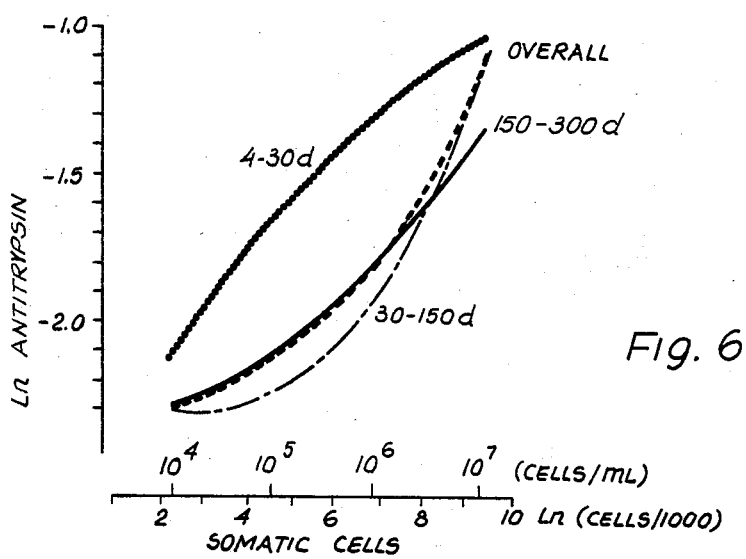
FIG. 6 illustrates the overall relationship between somatic cell count and antitrypsin in 1029 combined milk samples. The thinner lines show examples of how the stage of lactation affects the relationship. The upper curve representing the relationship during the first month of lactation deviates from the general picture. This is due to the presence of colostral inhibitors during early lactation (see FIG. 4).

The procedure is depicted in FIG. 3. The assay is adapted to the Multiskan* instrument measuring microtitration plates by vertical light path.
* Multiskan is the registered trademark of Eflab Oy products.

The sample wells on the microtitration plates included equal volumes (80 ul) of each supernate, trypsin working solution and BAPNA-substrate. A 100% control (without any antitrypsin) and the zero balance (without any trypsin) are included in each series of milk samples. The plates are left to incubate at room temperature for 3 hours, after which they are measured at 405 nm.

A standard curve is prepared either by using pure $\alpha_1$-protease-inhibitor solutions or dilution of bovine sera. Normal dairy milk contains about 0.5% of the respective serum content. Milk antitrypsin content (average) corresponds to 0.009 mg/ml pure $\alpha_1$-protease-inhibitor as estimated from its comparative trypsin-inhibitor capacity (bovine $\alpha_1$-protease-inhibitor obtained from Boehringer Mannheim GmbH, West Germany).

For practical purposes it is most convenient to use a dairy milk pool for the standard. It is easy to compare each individual sample with this average and evaluate whether the sample is "better" or "worse" than the average. Pooled milk can be conveniently obtained from dairies and this functions as an excellent standard for the assay. Inter-teat comparison is easy if the samples are obtained, processed and the results printed together. The lowest teat value should be taken as "healthy" and the others should be compared to this (in rare cases it is possible that all the quarters are inflammed).

By analyzing a number of standard curves prepared from sequential dilutions of $\alpha_1$-protease-inhibitor, serum or mastitic milk, a mathematical "fit" could be computed by knowing the 100% and 0% absorbences (FIG. 3, lower panel). This means that an assay can be delivered in a "kit" form without providing a serial dilution of standards. By including a standard sample (dairy pool) 100% control and 0-control among the samples, a pre-programmed desk computer can be used to indicate the antitrypsin content in relation to the standard sample. In FIG. 3, result 1 means that the content is the same as that in the standard sample and 2 means that the content doubles that of the standard.

The reproducability of the assay was determined from duplicate analyses. The reproducability was 6.0% of the mean at the linear part of the standard curve (25-75% inhibition, FIG. 3, lower panel). This figure includes inter-plate and day to day variations. The present assay was adapted to normal cow control material giving the mean value to be midway on the standard curve. However, if the material consists principally of mastitic milk samples, it might be wise to dilute the milk samples to have the values appear midway on the curve where the reading is more accurate.

When compared with the two other parameters of mastitis, the antitrypsin assay of the present invention shows an excellent correlation with the BSA-content as determined by radial immunodiffusion. The correlation with the somatic cell count was good excluding milk samples from early lactation. During the first weeks of lactation, milk contains colostral antitrypsin and the results from such samples should be evaluated with care. The same holds true to a lesser extent, for BSA and cell count as well.

The subject matter of this application is disclosed, in part, in an article entitled "Milk Antitrypsin Assay; A Novel Method of Screening For Mastitis" by applicant herein, in Volume 2 of the Proceedings of the Third International Symposium of the World Association of Veternary Laboratory Diagnosticians, pp. 571-576 (June 13-15, 1983). The entire disclosure of this article is hereby incorporated by reference.

I claim:

1. A method for the quantitative determination of mastitis in a cow comprising (a) coprecipitating casein, cream and $\alpha_2$-macroglobulin from a milk sample, (b) mixing said clear and substantially $\alpha_2$-macroglobulin free solution with a known amount of trypsin, (c) measuring the activity of the amount of trypsin which is present in said milk sample, and (d) comparing the obtained measurement of excess trypsin with a standard.

2. The method of claim 1 wherein the activity of trypsin excess is measured by reacting said trypsin with N-benzoylarginin-p-nitroanilide to form p-nitroaniline, and colorimetrically determining the amount of p-nitroaniline.

3. The method of claim 2 wherein said colorimetric determination is measured as a change in optical density which is directly proportional to the quantity of antitrypsin in the sample.

4. The method of claim 1 wherein said casein, cream and $\alpha_2$-macroglobulin are removed by precipitation with polyethylene glycol.

* * * * *